United States Patent [19]

Wang

[11] Patent Number: 4,766,906
[45] Date of Patent: Aug. 30, 1988

[54] BRONCHOSCOPIC NEEDLE ASSEMBLY

[76] Inventor: Ko Pen Wang, 813 Jamieson Rd., Lutherville, Md. 21093

[21] Appl. No.: 438,245

[22] Filed: Nov. 1, 1982

Related U.S. Application Data

[63] Continuation-in-part of Ser. No. 260,602, May 6, 1981, abandoned.

[51] Int. Cl.$^4$ ............................................. A61B 10/00
[52] U.S. Cl. ..................................... 128/753; 604/170
[58] Field of Search ................. 128/753, 754; 604/170

[56] References Cited

U.S. PATENT DOCUMENTS

| | | | |
|---|---|---|---|
| 2,623,521 | 12/1952 | Shaw | 128/754 |
| 3,438,373 | 4/1969 | Pannier, Jr. . | |
| 3,500,828 | 3/1970 | Podhora . | |
| 3,537,451 | 11/1970 | Beck . | |
| 3,598,108 | 8/1971 | Jamshidi et al. | 128/754 |
| 3,659,610 | 5/1972 | Cimber | 604/162 |
| 3,727,602 | 4/1973 | Hyden et al. | 128/753 |
| 3,747,812 | 7/1973 | Karman et al. | 604/220 |
| 3,855,561 | 5/1975 | Cami . | |
| 3,866,609 | 2/1975 | Sparks . | |
| 3,993,079 | 11/1976 | Gatztanondo . | |
| 4,006,744 | 2/1977 | Steer . | |
| 4,007,732 | 2/1977 | Kvavle et al. | 128/754 |
| 4,041,936 | 8/1977 | Carden . | |
| 4,052,989 | 10/1977 | Kline . | |
| 4,073,297 | 2/1978 | Kopp . | |
| 4,096,860 | 6/1978 | McLaughlin . | |
| 4,159,022 | 6/1979 | Pevsner | 604/159 |
| 4,181,132 | 1/1980 | Parks | 128/399 |
| 4,230,123 | 10/1980 | Hawkins, Jr. | 128/754 |
| 4,249,541 | 2/1981 | Pratt | 128/753 |

FOREIGN PATENT DOCUMENTS 193900  3/1923  United Kingdom ................ 128/347

OTHER PUBLICATIONS

Wang et al., "Bronchoscopic Needle Aspiration Biopsy of Paratrachael Tumors", Am. Review of Respiratory Disease, vol. 118 (1978).

Primary Examiner—Michael H. Thaler
Attorney, Agent, or Firm—Cushman, Darby & Cushman

[57] ABSTRACT

A completely flexible bronchoscopic needle assembly having fixed and retractable needle embodiments for use with a fiberoptic bronchoscope.

7 Claims, 2 Drawing Sheets

U.S. Patent  Aug. 30, 1988  Sheet 1 of 2  4,766,906
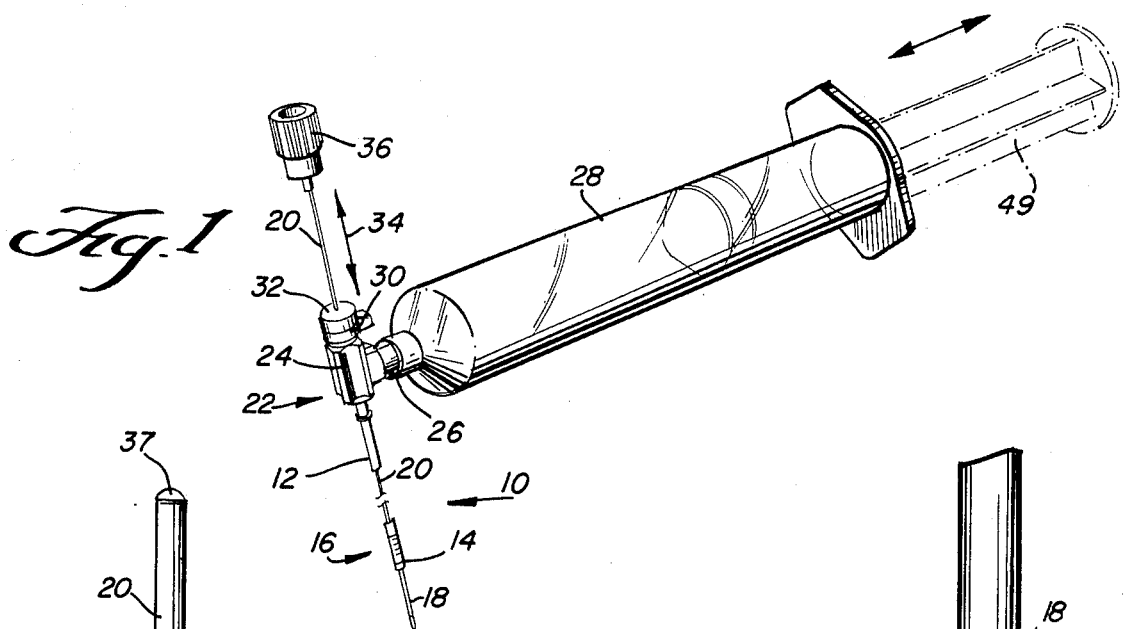
Fig. 1
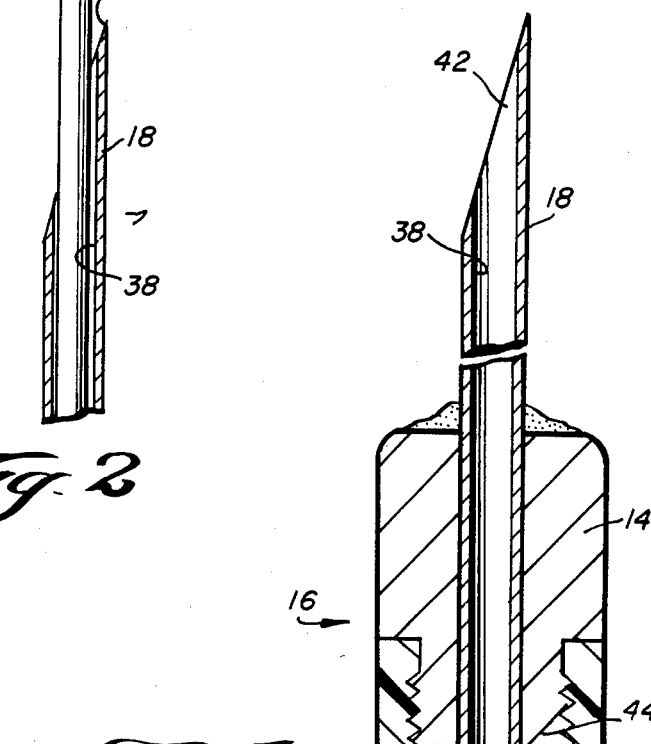
Fig. 2
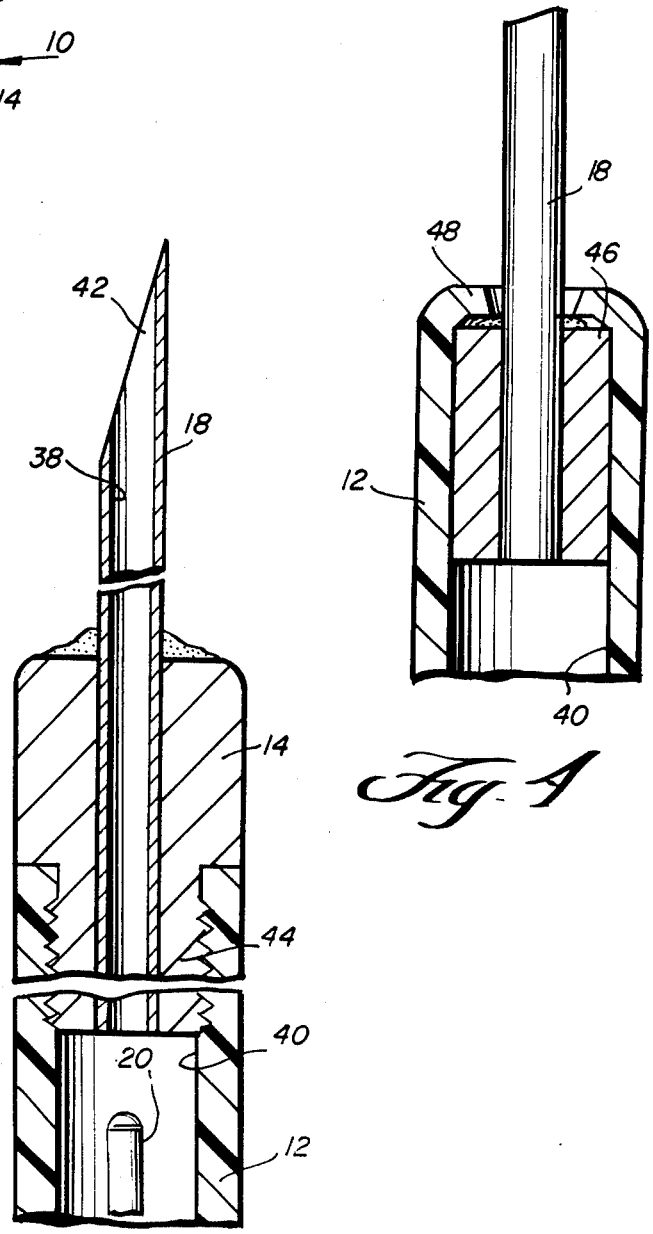
Fig. 3
Fig. 4

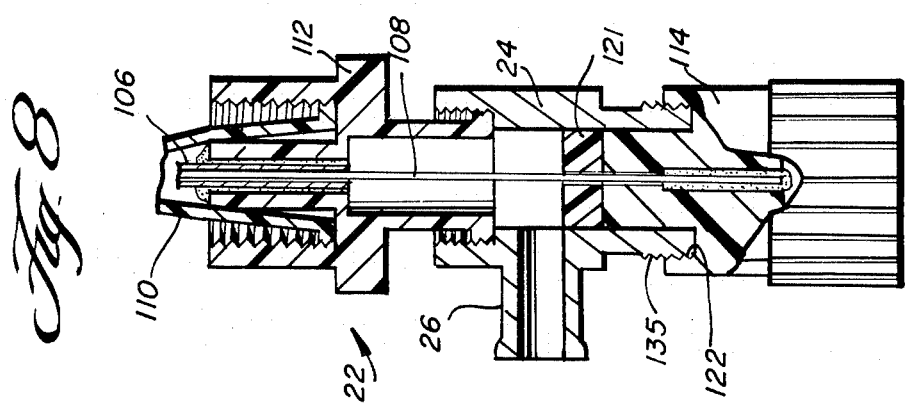
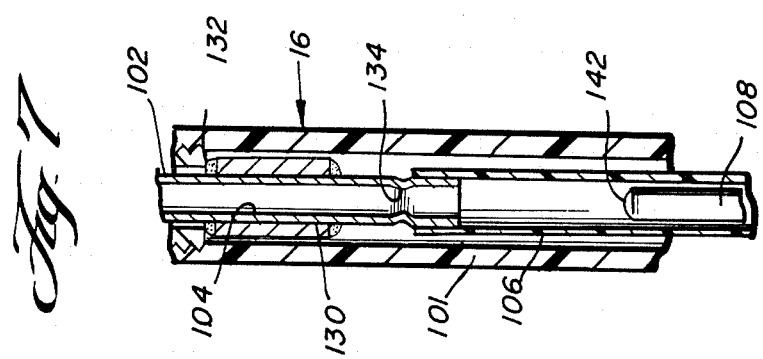
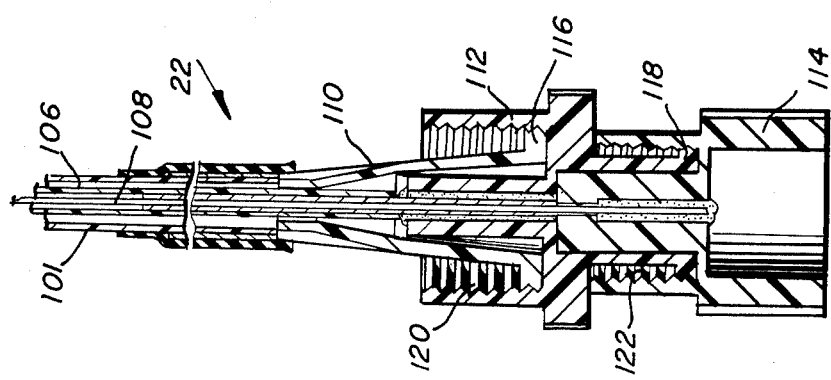
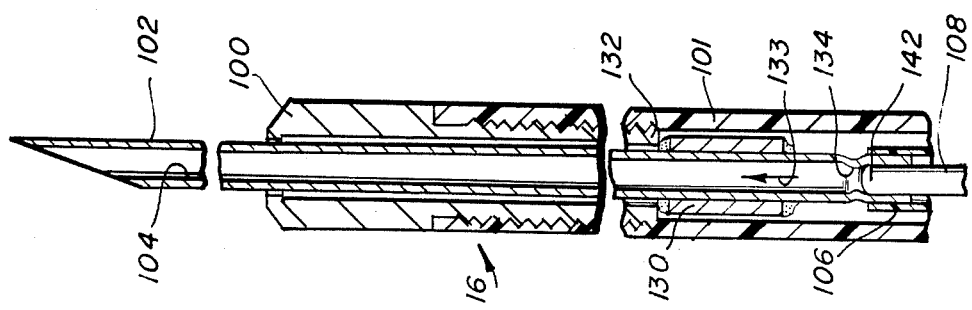

BRONCHOSCOPIC NEEDLE ASSEMBLY

RELATED APPLICATIONS

This application is a continuation-in-part of my co-pending U.S application Ser. No. 260,602 filed May 6, 1981, entitled "Bronchoscopic Needle", abandoned, the disclosure thereof being incorporated fully hereinto by reference.

BACKGROUND AND SUMMARY OF THE PRESENT INVENTION

In my copending application Ser. No. 260,602, a completely flexible bronchoscopic needle is disclosed wherein relatively non-invasive biopsy procedures can be performed utilizing the needle in combination with a fiberoptic bronchoscope. The attending physician inserts the bronchoscope into a predetermined one of the patient's natural orifices depending upon the particular organ desired to be biopsied. Thereafter, the needle assembly in accordance with tne invention of Ser. No. 260,602 is slideably inserted into a receiving passageway of the bronchoscope. The needle is urged into the tissue of the patient by a stabbing force exerted on the proximal end thereof (e.g. the end on the exterior of the patient's body) after the tubular needle portion comes into the bronchoscope's field of view. The bronchoscope enables the attending physician to accurately position the needle and to penetrate the exact location of the desired organ due to the viewing capabilities provided thereby. The present application is directed to improvements on the needle assembly disc in my co-pending application Ser. No. 260,602.

Heretofore, when biopsies were desired to be taken of the lymph nodes, for example, so as to aid in the diagnosis of carcinoma, the prior techniques would all typically utilize a substantially rigid needle and penetrate the body via percutaneous entry. For example, U.S. Pat. Nos. 3,630,192 and 3,628,524 each to Jamshidi disclose prior art biopsy needles suitable for percutaneous entry. U.S. Pat. No. 4,249,541 to Pratt discloses that a flexible biopsy instrument can be utilized in combination with a fiberoptic bronchoscope. However, Pratt's needle does not provide any locking means at the distal end thereof so that the needle may have a tendency to resist penetration of the desired tissue; e.g. the needle may retract somewhat into the bronchoscope passageway.

The needle assembly according to the present invention, however, solves such deficiencies by not only providing suitable protecting means which can at the desired time be removed to expose the sharp edge of the tubular needle so as to permit taking of biopsy samples but also ensures that the sharp needle will not resist penetration in to the tissue.

A particular problem in utilizing completely flexible bronchoscopic needles is to ensure that the rigid tubular needle (typically only about 2-3 cm in length) remains attached to the distal end of the needle assembly. Since the needle will penetrate the bronchial walls to access the lymph nodes or hard tumors therebehind, for example, there exists the possibility that upon withdrawal of the needle, the tubular needle portion will become totally separated from the assembly and remain lodged in the tissue. This would, of course, be a disastrous occurrence. Retrieval of the separated needle may be doubtful and would require the highest surgical skill. The present invention specifically addresses such a problem by providing a secure metal tip in the distal end of the catheter to which the needle is securely attached.

Furthermore, according to one embodiment of the present invention, the protective functions briefly mentioned above are realized by providing a tubular needle which is fully retractable within the outer catheter of the assembly, the smooth-shouldered distal end of the catheter thereby protecting both the fiberoptic bronchoscope and the patient from inadvertent needle damage. Thus, when it is desired to take a biopsy tissue sample, the retracted needle need only be extended beyond the distal end of the catheter. As previously noted, bronchial wall or hard tumor tissue will need to be penetrated and thus may present certain resistance to the needle. It is highly undesirable for the needle to inadvertently retract inside the catheter due to such resistance as this would not enable the attending physician to accomplish the desired organ biopsy. However, according to the present invention, secure locking engagement can be established so as to prevent inadvertent retraction of the needle into the catheter.

The above specifically noted advantages of the present invention and others will become more clear after careful consideration is given the detailed description of the preferred exemplary embodiments thereof.

BRIEF DESCRIPTION OF THE ACCOMPANYING DRAWINGS

Reference will be hereinafter made to the accompanying drawings wherein like reference numerals throughout the various figures denote like structural elements and wherein:

FIG. 1 is a representative perspective view of the biopsy needle assembly in accordance with the present invention;

FIG. 2 is a detailed cross-sectional view of the fixed needle embodiment of the present invention particularly showing the protective stylet in extension;

FIG. 3 is a detailed cross-sectional view of the distal end of the fixed needle embodiment of the present invention;

FIG. 4 is a detailed cross-sectional view of the distal end of an alternative means for fixing the needle in accordance with the FIG. 3 embodiment;

FIG. 5 is a detailed cross-sectional view of the distal end of the retractable needle embodiment of the present invention;

FIG. 6 is a detailed cross-sectional view of the proximal end of the FIG. 5 embodiment;

FIG. 7 is a detailed view similar to FIG. 5 showing the stylet partially retracted from the tubular needle; and FIG. 8 is a detailed view of another embodiment of the proximal end of the FIG. 5 embodiment showing in particular a leur lock in combination therewith.

DETAILED DESCRIPTION OF THE PREFERRED EXEMPLARY EMBODIMENTS

The present invention generally includes two embodiments hereinafter referred to as the fixed needle embodiment and the retractable needle embodiment. Each embodiment will be discussed in detail below.

FIG. 1, however, is representative of both embodiments of the present invention and the reader may wish to periodically refer thereto for an overall view of the present invention. As shown in FIG. 1, the biopsy needle assembly 10 generally includes an outer catheter 12, a metal tip 14 fixed to the distal end of catheter 12, and a rigid hollow needle 18 coaxial with tip 14. A flexible stylet 20 is slideably received with catheter 12 for a purpose which will become more clear from the discussion below.

The proximal end 22 of assembly 10 preferably includes a conventional two-directional leur lock 24, one of the directional nipples 26 for accepting an aspirating device, such as, a conventional syringe 28, the other directional nipple 30 being coaxially positioned relative to catheter 12. Covering nipple 30, I prefer to utilize an elastomeric seal 32 through which stylet 20 passes. Seal 32 is provided so as to permit all suction forces generated by syringe 28 to be communicated through needle 18 when it is desired to obtain biopsy tissue samples. Thus, no leakage will occur in the vicinity of stylet 20 where it passes through seal 32 yet reciprocal movement (arrow 34) of stylet 20 is permitted. A grippable cap 36 is fixed to the proximal end of stylet 20 so as to permit the attending physician to effect such reciprocal movement.

The reader should bear in mind that the needle assembly of the present invention is particularly well suited for use in combination with a flexible fiberoptic bronchoscope, and thus, must itself be completely flexible. As used herein and in the appended claims, the term "flexible" is meant to refer to axial flexion through an arc of 360° (e.g. axially looped). Thus, such flexibility permits the needle assembly to negotiate sharp turns even to the extent of permitting U-turns thereof.

In order to permit such flexibility I prefer to construct catheter 12 of a durable plastic material. Similarly, stylet 20 can be constructed of fine gauge metal or plastic wire, the flexibility thereof being substantially equal to the flexibility of the catheter 12 in which it is slideably received.

1. Fixed Needle Embodiment (FIGS. 2-4)

With the above noted generalities regarding the biopsy needle assembly 10 in mind, attention will now be directed to FIGS. 2-4 wherein one embodiment thereof (e.g. fixed needle embodiment) will be described in greater detail.

Stylet 20 is of sufficient length so that the smoothly rounded distal end 37 will extend beyond the sharp edge 42 of needle 18 (see FIG. 2). Preferably, stylet 20 extends about 1 to 3 cm beyond the sharp edge 42 of needle 18. In such a manner, the smoothly rounded end 37 of stylet 20 will protect the bronchoscope and the patient from inadvertent damage due to needle 18 during insertion of assembly 10. Once needle 18 is in the vicinity of the tissue area to be biopsied, stylet 20 is withdrawn so that end 37 is housed in hollow 38 of needle 18 thereby exposing sharp edge 42.

The diameter of stylet 20 is chosen so as to be closely fitted within needle cavity 38. While the structures of the present have been shown in a greatly exaggerated scale for clarity of presentation, the reader should realize that the needle 18 and stylet 20 are very small gauge. Thus, for all intents and purposes, the transition between the sharp edge 42 of needle 18 and the exterior surface of stylet 20 is substantially smooth when the latter is extended for protective functions.

FIG. 3 represents a detailed cross-sectional view of the distal end 16 of the fixed needle embodiment of the present invention. As shown, tubular needle 18 defines needle cavity 38 in communication with interior cavity 40 of catheter 12. Interior cavity 40 is preferably substantially cylindrical throughout its entire length. Needle cavity 38 is coaxially situated with interior cavity 40, the diameter of the former being preferably about one-third to about one-half that of the latter. Stylet 20, on the other hand, is sized so as to be closely received within needle cavity 18. Thus, stylet 20 is similarly about one-third to about one-half the diameter of interior cavity 12 so as to establish a significant annular space through which biopsy tissue and/or fluids can easily flow.

Needle 18 at its distal end defines a sharp edge 42 for penetrating a patient's tissue to obtain samples thereof while the proximal end thereof is rigidly fixed in tip 14. Needle 18 and tip 14 can be fixed to one another utilizing suitable solders, adhesives or like bonding agents, or alternatively, needle 18 can be integrally formed with tip 14.

Tip 14 is an important feature of the present invention in that it effects secure union between needle 18 and catheter 12 thereby preventing deleterious separation thereof. Tip 14 is preferably constructed of a hard metal (e.g. stainless steel) or hard plastic material.

In accordance with the embodiment of FIG. 3, tip 14 is provided with a male threaded member 44 so that when threadingly inserted into interior cavity 40, the male threads on member 44 act as a tapping tool to cut corresponding female threads into catheter 12. Thus, a self-tapping system is established whereby axial forces will be resisted thereby preventing separation of tip 14, and thus needle 18, from catheter 12.

A second embodiment of the distal end 16 of the fixed needle embodiment is depicted in FIG. 4. In the FIG. 4 embodiment, tip 46 is similarly rigidly fixed to needle 18. However, in order to resist axial forces, I prefer to dimension the exterior diameter of tip 46 slightly larger than the diameter of interior cavity 40 so that a secure, press-fitting relationship is established. The terminal end of catheter 12 may then be heat-formed so that upon cooling, the distal end of catheter 12 is formed with an inward flange 48 thereby at least partially closing interior cavity 40 over tip 46. In order to effect such closure, tip 46 must be recessed within cavity 40. Thus, partial closure of the distal end of catheter 12 will resist axial forces in a direction tending to separate needle 18 from catheter 12 while the press-fitting relationship between tip 46 and catheter 12 resists axial forces in a direction tending to push needle 18 into cavity 40.

In practice, the needle assembly 10 having the fixed needle embodiment of the present invention is inserted into the flexible fiberoptic bronchoscope with stylet 20 extended beyond sharp edge 42 so as to provide protective functions. When the desired tissue area is located, stylet 20 is withdrawn to a position below sharp edge 42 and the needle 18 is penetrated into the tissue area by a stabbing motion. When the biopsy material is desired to be withdrawn, plunger 49 of syringe 28 is pulled thereby creating a significant suction force. Since stylet 20 is sized so as to be closely fitted within hollow 38 of needle 18, the biopsy material will not pass therethrough when stylet 20 is housed with hollow 38. However, when stylet 20 is withdrawn completely from hollow 38, a significant space is provided with enables biopsy material to flow therethrough due to the suction force and be deposited into syringe 28. Thereafter, the biopsy material can be examined for diagnostic purposes.

A significant advantage of utilizing the fixed needle embodiment of the present invention is that stylet 20 need not be completely removed from catheter 12 so as to permit aspiration. Thus, merely withdrawing stylet 20 so that end 37 is about 1-2 cm interiorly removed from hollow 38 will permit the biopsy tissue and/or fluids to flow therearound in the annular space.

2. The Retractable Needle Embodiment (FIGS. 5-8)

Once again the reader is directed to the general discussion regarding assembly 10 as noted above with reference to FIG. 1. Such general structures previously noted can be modified in accordance with a second embodiment (e.g. retractable needle embodiment) of the present invention, which embodiment will now be described in greater detail with reference to accompanying FIGS. 5-8.

The distal end 16 of the retractable needle embodiment (see FIGS. 5 and 7) includes a tip 100 threadably coupled to outer catheter 101 in a manner similar to that described above with reference to tip 14 and catheter 12 in FIG. 2. However, needle 102 (defining needle cavity 104) is not fixed to tip 100, but rather is reciprocably moveable therein. Needle 102 is fixed to and carried with inner catheter 106 while stylet 108 is slideably received in inner catheter 106.

The proximal end 22 of assembly 10 in accordance with the retractable needle embodiment (see FIGS. 6 and 8) preferably includes an outer catheter cap 110 fixed to outer catheter 101, an inner catheter cap 112 fixed to inner catheter 106, and a stylet cap 114 fixed to stylet 108. In such a manner, independent reciprocal movement of inner catheter 106 and stylet 108 relative outer catheter 101 is achieved. Mutual locking of caps 110, 112 and 114 can be provided by conventional threading engagement of male threads 116 and 118 on caps 110 and 112, respectively, with cooperating female threads 120 and 122 defined on caps 112 and 114, respectively.

Preferably, a conventional two-directional leur lock 30 having an elastomeric plug 121 (see FIG. 8) can be provided intermediate caps 112 and 114 to permit similar aspirating functions as previously described with reference to assembly 10 depicted in FIG. 1. In the retractable needle embodiment, however, aspiration is effected through the cavity of inner catheter 106 with stylet 108 completely removed, or alternatively, the inner catheter 106 can be sized so as to define an annular space with stylet 108 through which biopsy material can flow.

An important feature of the retractable needle embodiment of the present invention is that means are provided for maintaining a biasing force on needle 102 so as to resist compression forces tending to retract needle 102 into catheter 101. Such means are extremely important when consideration is given to the fact that oftentimes relatively tough tissue must be penetrated (e.g. bronchial walls or hard tumors) in order to obtain the desired biopsy material. Thus, such tough tissue may exert a sufficient amount of resistance against needle 102 so as to cause at least partial retraction thereof into outer catheter 101. Such partial retraction of needle 102 is to be strictly avoided. For example, should partial retraction occur, the attending physician will not be able to completely penetrate the bronchial wall in order to obtain a biopsy sample of the lymph nodes therebehind. This may lead to a misdiagnosis of the patient's ailment, for example, as the tissue sample which will be obtained will not be of the diseased lymph node, but rather will be of the undiseased bronchial wall.

In order to prevent such occurrences, I prefer to provide needle 102 with a fixed hub 130 which acts as a limit member to limit the extended travel of needle 102. The limiting functions of hub 130 are achieved by ensuring that it bears against the proximal end 132 of tip 100 and thus hub 130 should also be constructed of a hard material, such as, stainless steel or the like.

To ensure that hub 130 securely bears against the proximal end 132 of tip 100, a biasing force (arrow 133) is applied by stylet 108 acting against recessed surfaces 134 formed in needle 102. Recessed surfaces 134 are preferably formed merely by crimping a predetermined portion of needle 102 so as to reduce the diameter of needle cavity 104 at such portion yet will still be of sufficient diameter to permit biopsy material to pass therethrough. Alternatively, integral stop members could be formed at a predetermined location in needle cavity 104 or a flange could be provided on the distal end of stylet 108.

The magnitude of biasing force 133 is determined by providing stylet 108 with sufficient axial length so that it is longer (on the order of about 1 to about 3 cm) than the axial length of assembly 10 as measured between recessed surfaces 134 and the proximal end of assembly 10. Thus, upon first contact of the rounded distal end 142 of stylet 108 with recessed surfaces 134, a predetermined excess of stylet 108 will be apparent at the proximal end of assembly 10. Upon removal of such excess by forcing cap 114 in a direction towards distal end 16, a biasing force of sufficient magnitude will be exerted against needle 102 to ensure that hub 130 bears against proximal end 132 of tip 100 thereby establishing rigid extension of needle 102 to prevent undesired retraction thereof.

Secure locking engagement between threads 118 and 122 of caps 112 and 114, respectively, maintaining biasing force (arrow 133) without requiring manual retention of the attending physician. Similarly, threads 135 on leur lock 24 can be provided, if utilized, to maintain the biasing force, threads 135 thereby cooperating with threads 122 of cap 114.

Of course, when desired, needle 102 may be simply retracted by removing such biasing force and retracting inner catheter 106 thereby carrying needle 102 along with it. In such a manner, the bronchoscope and patient can be protected by inserting assembly 10 having needle 102 in a retracted position, yet will enable the attending physician to perform the required biopsy with needle 102 in the securely extended position as previously noted.

Thus, both embodiments of the present invention protect the bronchoscope and patient from inadvertent needle damage, yet permit the attending physician to reliably perform the desired tissue biopsy. Accordingly, while the present invention has been herein described in what is presently conceived to be the most preferred embodiments thereof, those in the art may appreciate that many modifications may be made hereof, which modifications shall be accorded the broadest interpretation of the appended claims so as to encompass all equivalent assemblies, structures and/or devices.

What I claim is:

1. A completely flexible bronchoscopic needle assembly for use with a flexible bronchoscope comprising:

an elongated axially flexible catheter having proximal and distal ends and defining an interior cavity therebetween;

a hard tip including means for rigidly fixing said tip to said catheter distal end;

a hollow needle rigidly and coaxially fixed to said tip, said needle defining a sharp edge extended away from said tip, the hollow of said needle being in communication with and having a cross-sectional diameter less than said interior cavity, wherein said tip effects secure union between said rigid needle and said flexible catheter by virtue of said fixing means to prevent separation of said rigid needle and said flexible catheter; and protecting means reciprocably moveable within said catheter and said hollow needle for protecting said bronchoscope and said patient from inadvertent damage due to said sharp edge, said protecting means including an elongated flexible stylet having a smoothly rounded distal end and being of sufficient length to enable said smoothly rounded distal end to be extendable beyond said sharp edge a predetermined dimension so as to substantially mask said sharp edge to prevent inadvertent damage thereby, the diameter of said stylet closely fitting within said hollow of said needle thereby defining with said interior cavity a substantially annular space through which biopsy material can flow.

2. An assembly as in claim 1 further comprising means in communication with said annular space for permitting aspiration of said biopsy material therethrough.

3. An assembly as in claim 2 wherein said aspiration means comprises:
 a leur lock including a first nipple defining a central chamber in coaxial communication with said annular space, and a second nipple defining an aspirating chamber in communication with said central chamber,
 sealing means covering said first nipple, the proximal end portion of said stylet being slideably moveable through and being sealed by said sealing means; and
 syringe means for creating a negative pressure to aspirate said biopsy material through said annular space and be deposited within said syringe means.

4. An assembly as in claim 1 wherein said fixing means includes means defining male threads for being threadably engaged with said catheter.

5. An assembly as in claim 1 wherein said tip is recessed and press-fitted within said cavity, said fixing means including flange means integrally formed on the distal end of said cavity, said flange means at least partially closing said cavity thereby at least partially covering said tip recessed therein.

6. A completely flexible bronchoscopic needle assembly for use with a flexible bronchoscope comprising:
 an elongated flexible catheter having proximal and distal ends and defining an interior cavity therebetween;
 a hard tip including means for rigidly fixing said tip to said catheter distal end, said fixing means including means defining male threads for being threadably engaged with said catheter;
 a hollow needle rigidly and coaxially fixed to said tip, said needle defining a sharp edge extended away from said tip, the hollow of said needle being in communication with and having a cross-sectional diameter less than said interior cavity; and protecting means reciprocably moveable within said cathether and said hollow needle for protecting said bronchoscope and said patient from inadvertent damage due to said sharp edge, said protecting means including an elongated flexible stylet having a smoothly rounded distal end and being of sufficient length to enable said smoothly rounded distal end to be extendable beyond said sharp edge a predetermined dimension so as to substantially mask said sharp edge to prevent inadvertent damage thereby, the diameter of said stylet closely fitting within said hollow of said needle thereby defining with said interior cavity a substantially annular space through which biopsy material can flow.

7. A completely flexible bronchoscopic needle assembly for use with a flexible bronchoscope comprising:
 an elongated flexible catheter having proximal and distal ends and defining an interior cavity therebetween;
 a hard tip including means for rigidly fixing said tip to said catheter distal end;
 a hollow needle rigidly and coaxially fixed to said tip, said needle defining a sharp edge extended away from said tip, the hollow of said needle being in communication with and having a cross-sectional diameter less than said interior cavity; and protecting means reciprocably moveable within said cathether and said hollow needle for protecting said bronchoscope and said patient from inadvertent damage due to said sharp edge, said protecting means including an elongated flexible stylet having a smoothly rounded distal end and being of sufficient length to enable said smoothly rounded distal end to be extendable beyond said sharp edge a predetermined dimension so as to substantially mask said sharp edge to prevent inadvertent damage thereby, the diameter of said stylet closely fitting within said hollow of said needle thereby defining with said interior cavity a substantially annular space through which biopsy material can flow; and wherein said tip is recessed and press-fitted within said cavity, said fixing means including flange means integrally formed on the distal end of said cavity, said flange means at least partially closing said cavity thereby at least partially covering said tip recessed therein.

* * * * *